(12) United States Patent
Janusson et al.

(10) Patent No.: US 6,626,952 B2
(45) Date of Patent: Sep. 30, 2003

(54) PREFORM FOR MAKING PROSTHETIC SUSPENSION SLEEVE

(75) Inventors: Hilmar Janusson, Seltjarnarnesi (IS); Freygarour Thorsteinsson, Reykjavik (IS); Sigurour A. Asgeirsson, Kopavogur (IS); Palmi Einarsson, Kopavogur (IS)

(73) Assignee: Ossur HF, Reykjavik (IS)

( * ) Notice: Subject to any disclaimer, the term of this patent is extended or adjusted under 35 U.S.C. 154(b) by 0 days.

(21) Appl. No.: 10/279,820

(22) Filed: Oct. 25, 2002

(65) Prior Publication Data
US 2003/0113494 A1 Jun. 19, 2003

Related U.S. Application Data

(62) Division of application No. 09/805,126, filed on Mar. 14, 2001, now Pat. No. 6,485,776.
(60) Provisional application No. 60/189,478, filed on Mar. 15, 2000.

(51) Int. Cl.$^7$ ............................... A61F 2/60; A61F 2/80
(52) U.S. Cl. ............................................ 623/36; 623/33
(58) Field of Search .............................. 623/33, 34, 35, 623/36, 32; 2/239

(56) References Cited

U.S. PATENT DOCUMENTS

| | | |
|---|---|---|
| 4,041,198 A | 8/1977 | McPherson |
| 4,347,204 A | 8/1982 | Takagi et al. |
| 4,600,615 A | 7/1986 | Hyodo et al. |
| 4,635,626 A | 1/1987 | Lerman |
| 4,698,196 A | 10/1987 | Fabian |
| 4,859,380 A | 8/1989 | Ogata |
| 4,923,474 A | 5/1990 | Klasson et al. |
| 5,376,129 A | 12/1994 | Faulkner et al. |
| 5,571,208 A | 11/1996 | Caspers |
| 5,593,454 A * | 1/1997 | Helmy .................... 623/32 |
| 5,603,122 A * | 2/1997 | Kania ..................... 2/239 |
| 5,728,168 A | 3/1998 | Laghi et al. |
| 5,885,674 A | 3/1999 | Maemoto et al. |
| 5,899,636 A | 5/1999 | Toyoda et al. |
| 6,136,039 A | 10/2000 | Kristinsson et al. |
| 6,149,690 A * | 11/2000 | Belzidsky ................ 623/32 |
| 6,231,617 B1 * | 5/2001 | Fay ........................ 623/36 |
| 6,454,812 B1 * | 9/2002 | Laghi ..................... 623/36 |

FOREIGN PATENT DOCUMENTS

JP   1221223   9/1989

\* cited by examiner

*Primary Examiner*—Bruce Snow
(74) *Attorney, Agent, or Firm*—Bacon & Thomas, PLLC (57) ABSTRACT

A preform for a prosthetic suspension sleeve includes a tubular sleeve made of an elasticized fabric that is coated on its inner wall with an uninterrupted cured silicone elastomer layer and having a distal end cap molded on and closing a distal end of the elasticized fabric sleeve. A tubular matrix reinforcement element is secured coaxially to the distal end of the sleeve with a portion embedded in the distal end cap and a portion extending freely within a distal end area of the sleeve. Another embodiment of a preform includes a tubular sleeve of elasticized fabric with a tubular matrix reinforcement element secured coaxially to the distal end of the sleeve, the matrix reinforcement element including interlocking fibers arranged so that the reinforcement element is porous and strongly resists elongation in a sleeve longitudinal direction but is readily elastically stretchable in transverse directions.

6 Claims, 9 Drawing Sheets

PREFORM FOR MAKING PROSTHETIC SUSPENSION SLEEVE

CROSS-REFERENCE TO PROVISIONAL APPLICATION

This application is a divisional of prior U.S. application Ser. No. 09/805,126 filed Mar. 14, 2001, now U.S. Pat. No. 6,485,776, which claims the benefit of Provisional Application No. 60/189,478 filed Mar. 15, 2000 under 35 U.S.C. §119(e)(1).

1. FIELD OF THE INVENTION

This invention relates to the process and apparatus for making prosthetic suction liners and coating tubular substrates.

2. BACKGROUND OF THE INVENTION

Prosthetic suction liners have been described in U.S. Pat. No. 4,923,474 granted to Klasson and Kristinsson on May 8, 1990; U.S. Pat. No. 5,728,168 granted Mar. 17, 1998 to Laghi et al.; and U.S. Pat. No. 5,830,237 granted to Kania Nov. 3, 1998.

The original suction liner as described in U.S. Pat. No. 4,923,474 was formed of a silicone elastomer and was adapted to the rolled over residual limb of a prosthetic user in a manner fully described in the patent.

The manufacturing process for making suction liners with a fabric exterior covering adhered to one or more cured elastomer inner layers typically involves multiple injection molding procedures and possibly laminating procedures that are designed to build-up the various layers constituting the suction liner. Obtaining an intimate bond between the silicone, and fabric layers is particularly important, particularly when it is necessary to maintain full elasticity of the suction liner to enable it to closely fit over and conform to a residual limb of a prosthetic user.

The process is more complicated when a distal prosthetic connector fitting must be incorporated in the distal end of the suction liner, particularly when an injection molding procedure is utilized.

Injection molding procedures are time consuming and require complex equipment to ensure accurate shapes and thicknesses of various size suction liners. Injection molding thick, soft elastomeric layers on the inner surfaces of suction liners also present a challenge using injection molding techniques.

Prior art procedures for continuously coating tubular substrates with a cured elastomer coating or film involve many different procedures that tend to be expensive and time consuming. It is highly desirable to continuously coat tubular substrates with an elastomer layer intimately bonded or adhered to the substrate in a convenient, low cost procedure, particularly where the substrate is an elasticized, porous fabric.

BRIEF SUMMARY OF THE INVENTION

The invention relates to a process for forming a generally conical, close ended suction liner having a fabric outer covering, a thin cured silicone elastomer coating preferably provided on the interior surface of the fabric and a cured silicone elastomer lining adjacent the intermediate silicone coating. The prosthetic suction liner is formed with a distal end cap in which a prosthetic "umbrella" connector is embedded at the distal end of the suction liner using a process according to the invention described herein. The prosthetic connector is exposed in a central portion to provide access to a prosthetic pin connector in a conventional manner. An optional reinforcement layer may be embedded in the innermost silicone elastomer layer using the inventive process to restrict axial elongation of the distal end portion of the suction liner while permitting lateral distension of the liner material in that portion of the liner in which the reinforcement material is embedded in the silicone elastomer layer.

One aspect of the inventive process involves providing a cylindrical tubular length of elasticized fabric that is stretchable both longitudinally and laterally relative to the axis of the tube; coating the inner surface of the fabric tube with a continuous, thin cured silicone elastomer that partially penetrates and adheres strongly to the fabric but does not extend through the full fabric thickness; optionally attaching a tubular length of reinforcement matrix material to one end of the coated tubular fabric; placing the tubular length of fabric and the optional reinforcement in a molding device; placing the umbrella prosthetic connector element in the molding device; molding and curing a silicone elastomer distal end cap over one end of the tubular length of coated fabric and the optional reinforcement matrix so as to embed the umbrella prosthetic connector in the distal end cap silicone material while bonding the distal end cap to the end of the tubular length of fabric and the optional reinforcement matrix; removing the tubular length of fabric with the molded distal end cap from the molding device and inserting a premeasured quantity of uncured silicone resin that will form an inner layer of the liner into the closed end of the fabric tube and end cap; inserting the fabric tube with the premeasured quantity of uncured resin and the distal end cap into a female mold cavity having a defined peripheral contour corresponding to a desired outer peripheral contour of the prosthetic suction liner; advancing a male mold member having an external contour corresponding to the desired inner contour of the suction liner into the interior of the tubular fabric and distal end cap assembly from its open end to cold forge the uncured silicone elastomer over the full length of a cavity defined between the male and female molds to fully form the innermost silicone elastomer layer to a desired contour and thickness and carrying out a preliminary cure of the inner most silicone elastomer in the forging device; removing the formed assembly of tubular fabric and partially cured silicone elastomer layer from the forming device and fully curing the innermost silicone elastomer layer.

Apparatus for carrying out the process includes a continuous film casting device configured to continuously cast an uncured elastomer film coating on a tubular substrate using sub-atmospheric suction to draw the film to the surface of the fabric substrate; and a heater in series with the continuous film casting apparatus arranged to cure the cast elastomer film continuously during the coating process to thereby produce a continuous tubular length of substrate coated on one surface thereof with a cured elastomer film.

When the apparatus is used to apply an elastomer coating to a porous material such as an elasticized fabric, the suction applied during casting of the uncured elastomer film is adjusted so that the film partially embeds itself in the intersices or pores of the fabric while avoiding complete penetration of the elastomer throughout the fabric thickness. This leaves the opposed surface of the fabric free of elastomer while producing a continuous sealing film of elastomer on the first surface of the tubular length of fabric.

During curing, the tension applied to the coated substrate is adjusted to produce optimum qualities for the coated length of substrate that are appropriate for the thus produced product or any subsequent use of the coated substrate in a manufacturing procedure in which the coated substrate is formed into an end product.

The thus coated tubular length of substrate may be reversed with the cured elastomer coating on the inside of the substrate. The tubular coated substrate may then be cut to lengths corresponding approximately to individual lengths of products to be made with the coated lengths of substrate and a tubular matrix of reinforcement material may be attached to one end of the end of the tubular length of substrate for use, for example, in a prosthetic suction liner.

As described previously, a distal end cap may be molded to the one end of a tubular length of coated elasticized fabric substrate with a prosthetic connector fitting or umbrella embedded in the distal end cap.

In a specific example wherein it is desired to use such a continuous coated tubular substrate in a process for making a prosthetic suction liner, the substrate comprises a tubular elasticized fabric such as circular knit fabric that is distensible both lengthwise and widthwise and the elastomer is constituted of a silicone elastomer formulated so that it may be cast as a continuous film in its uncured condition in a temperature range that is practical. The coated fabric maintains its elasticity due to the elasticity of the silicone elastomer in its cured condition. The surface of the cured silicone film may be left in a somewhat tacky condition so as to be readily bondable to a subsequent silicone elastomer layer.

The cold forging apparatus includes a female die that preferably includes suction devices to draw the fabric tube into intimate contact with the interior walls of the female die prior to the advancement of the male member into the female die. The male die member formed in accordance with a desired inner profile of the innermost silicone elastomer layer of the suction liner, is advanced into the uncured silicone elastomer previously deposited into the closed end of the fabric and distal end cap assembly so the elastomer is forced to flow longitudinally through a cavity that is formed between the female die and the male die member from the closed end of the suction liner to the proximal open end thereof. The procedure may be referred to as a cold forging process for convenience.

The rate of advancement of the male die member is controlled to permit complete flow of the uncured silicone elastomer throughout the cavity provided between the male and female die members, particularly when the gap between the male and female die members varies along the length of the molding device.

A guide pin may be inserted into the prosthetic connector element embedded in the distal end cap of the pre-formed tubular length of coated fabric, distal end cap and prosthetic connector. The female die includes an aperture at its distal end arranged to receive the guide pin to thereby center and locate the length of coated fabric and distal end cap in the female die before the male die member is advanced into the female die to cold forge the uncured silicone elastomer resin into the die cavity between the male and female die members.

The male and female dies may be heated to perform a preliminary curing of the silicone elastomer of the silicone elastomer in the mold cavity before the laminated assembly of elasticized fabric, thin coating of silicone elastomer and final inner layer of silicone elastomer are removed from the die.

The process and apparatus constituting the inventive subject matter will be described in more detail in the drawings and description that follow.

DETAILED DESCRIPTION OF PREFERRED EMBODIMENTS OF THE INVENTION

Figures 1, 2, 3:
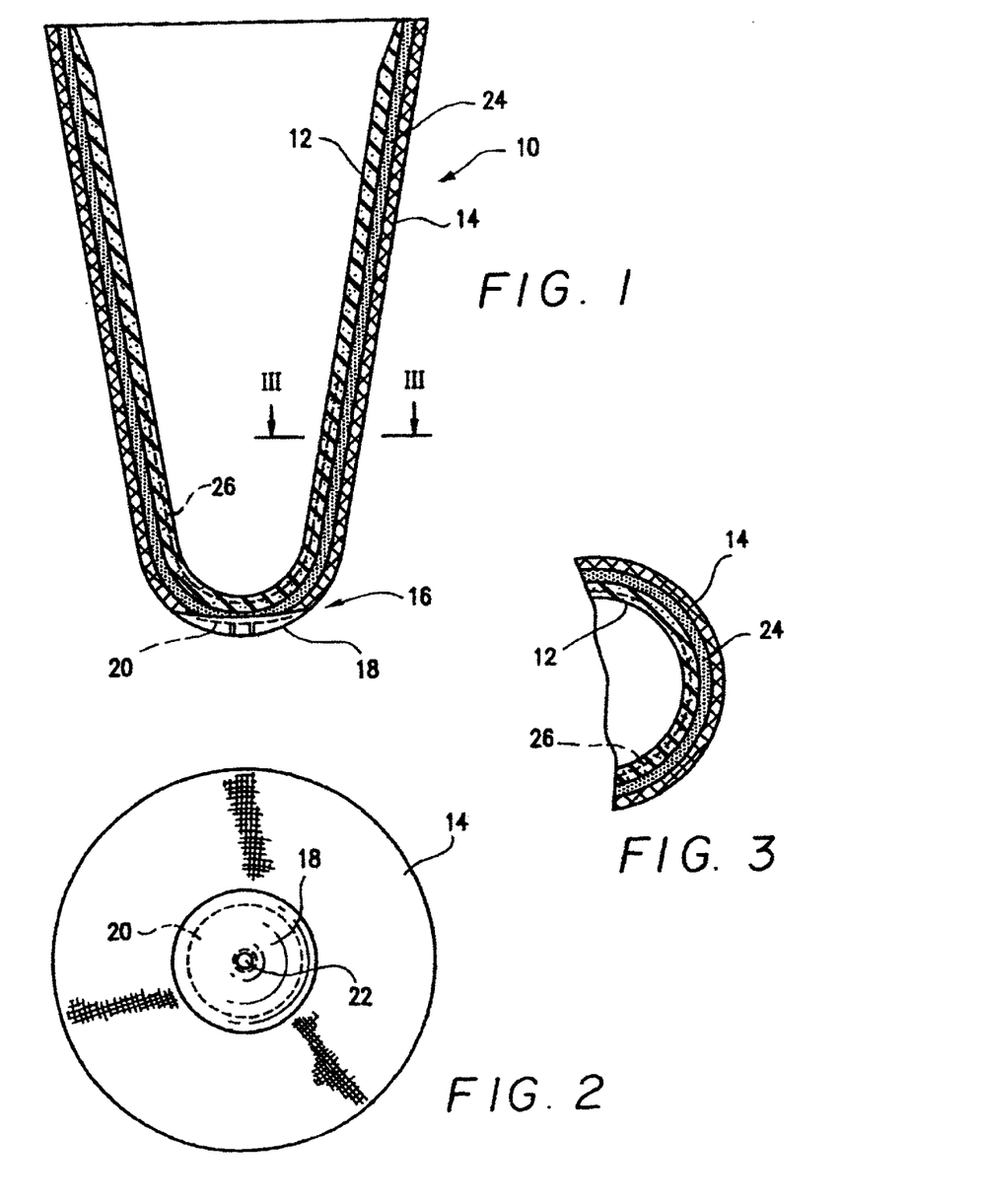
FIG. 1 is a longitudinal section view of a suction liner formed in accordance with the process according to the present invention.
FIG. 2 is a distal end view of the suction liner shown in FIG. 1.
FIG. 3 is a section view taken along line III—III of FIG. 1.

FIG. 1 schematically illustrates in a cross-section view a prosthetic suction liner 10 that may be formed using the process and apparatus described herein. The liner is formed in part of a composite elastic material 12 on its interior surface and an elasticized fabric layer 14 on its exterior surface at least up to its distal end area 16, where a distal end cap 18 having embedded therein a rigid prosthetic connector 20 formed, for example, of aluminum or other metal, or rigid plastic such as Nylon, is provided.

The liner 10 is formed as a close ended tapered tubular element, as is conventional for such suction liners. The distal end cap 18 firmly joins the prosthetic connector 20 to the suction liner 10 while providing a cushioning and stabilizing surface at the distal end of the liner. The prosthetic connector 20 includes preferably a threaded aperture 22 for providing access to a threaded prosthetic pin connector in a manner well known in the art.

FIG. 2 shows the suction liner in an end view as seen from the distal end of the liner.

FIG. 3 is a cross-section view taken along line III—III of FIG. 1 and shows the composite elastic material 12, the elasticized fabric layer 14, and a second thin continuous coating of silicone elastomer material 24 partially embedded in the elasticized fabric layer 14 while not completely penetrating the fabric layer. The intermediate coating 24 is bonded on its opposite side to the composite elastic material 12, whereby the entire assembly of composite elastic material 12, elastomer coating 24 and elasticized fabric 14 is at least freely radially elastically distendable.

The composite elastic material layer 12 may have embedded therein a matrix of reinforcement fibers 26 or other suitable reinforcement having properties such that the composite elastic layer 12 strongly resists longitudinal elongation while it is freely distendable radially of the suction liner for use in liner applications when axial elongation of the liner must be limited. A circular knit glass fiber or Nylon material is preferred.

Figure 4:
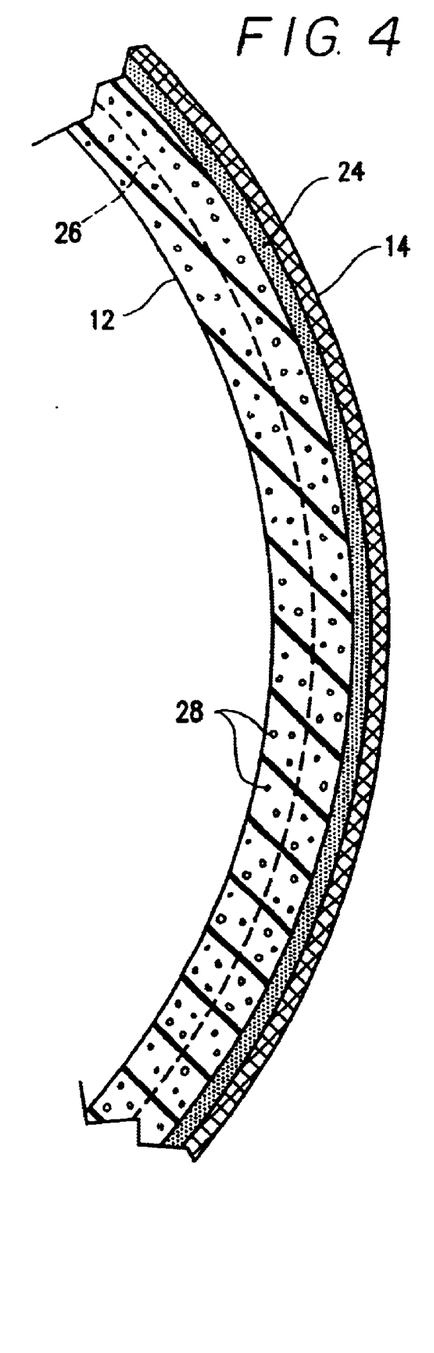
FIG. 4 is an enlarged view of FIG. 3 to show the details of the suction liner side wall.

FIG. 4 is an enlarged view of FIG. 3 and shows the composite elastic material made in accordance with the present invention in more detail as well as a wall section of suction liner 40 made with such material. Layer 12 may be a novel composite elastic material comprising a cured silicone elastomer containing silicone oil and hollow microspheres 28 dispersed throughout the silicone elastomer layer.

The illustrations in FIGS. 3 and 4 also show the reinforcement matrix fibers 26 embedded in the silicone elastomer layer, but it should be understood that such reinforcement fibers are optional and extend over a distal portion of the liner to limit axial distension of the liner in such distal portion. The reinforcement fibers 26, of course, do not constitute a portion of the basic composite elastic material described above.

More specifically, the composite elastic material layer 12 itself is regarded as a new and useful proprietary composite elastic material independently of the fibers 28, the outer fabric 14 and the intermediate coating.

In a preferred example, the composite elastic material 12 is formed principally of a silicone elastomer obtainable from NuSil Technology of Carpinteria, Calif. under Product Designation CF13-2188. For a fuller description of the silicone material, reference may be made to pending U.S. Pat. No. 6,136,039 granted Oct. 24, 2000 owned by the assignee of the invention described herein.

Embedded within the silicone elastomer material of layer 12 are hollow thermoplastic microspheres consisting of a polymeric shell with an enclosed blowing agent. The specific thermoplastic microspheres utilized in this example of the invention are expanded microspheres obtained from AKZO NOBEL of Sweden under the trade name EXPANCEL®, Product No. 551DE.

The microspheres 28 preferably have a density of 0.005 g/cm$^3$ to 1.25 g/cm$^3$, preferably 0.05 g/cm$^3$.

For a fuller understanding of the formulation of EXPANCEL® microspheres, reference may be made to EXPANCEL® Technical Bulletin 29 and the EXPANCEL® product specification and material safety data sheets, all of which are available from AKZO NOBEL, S-850, 13 Sundsvall, Sweden.

The silicone oil included in the composite elastic material may be obtained from GE Bayer Silicones GmbH of D 51 368 Leverkusen, Germany under Product Name Baysilone Fluid M350.

In a preferred form, the composite elastic layer 12 comprises 50–99.4% by weight of silicone elastomer, preferably 77.25%; 0.5–45% by weight of silicone oil, preferably 10%; and 0.1–5% by weight of microspheres, preferably 0.75%.

The composite elastic layer 12 also may include one or more skin treatment agents blended into the silicone elastomer, for example Vaseline and aloe vera. In a preferred example, up to 20% by weight of the composite elastic layer, preferably 11.9%, may be Vaseline and up to 3%, preferably 0.1%, may be a secondary skin treatment agent such as aloe vera.

While EXPANCEL® hollow microspheres as described above are preferred, it should be understood that other hollow microspheres having a density range of 0.005 g/cm$^3$ to 1.24 g/cm$^3$, preferably 0.05 g/cm$^3$, could be used.

When prepared as described above, a preferred embodiment of the composite elastic layer will have a density of 0.5 g/cm$^3$ to 1.3 g/cm$^3$, preferably 0.94 g/cm$^3$; a tensile strength greater than 0.1 Pa, preferably greater than 0.5 Pa; a durometer (00) of 13 to 62, preferably 22; a 100% modulus of 5 kPa to 250, preferably 20 kPa; and a compression set of 0 to 30, preferably 8.

It should be understood that different or additional skin treating agents may be utilized, depending upon the skin condition to be treated by the skin treating agent. For use as a typical suction sleeve, Vaseline and aloe vera are believed to provide good properties for the composite elastic layer that typically directly contacts or is in close proximity with the skin of a prosthetic user.

When the composite elastic material 12 is laminated or bonded with an elasticized textile layer 14, such layer 14, in a preferred embodiment, may be described as a Supplex Nylon circular knit of 87% Nylon, 13% Spandex fibers using 28 needles per 2.5 cm having a weight per square yard of 6.9 ozs. and a weight per linear yard of 12 ozs. Such a Supplex Nylon is obtainable from Agmont Inc. of Montreal, Quebec, Canada under Style Name 5095. This material has a finished width of 60" (152.4 cm) and is substantially elastically distendable along its length and width in a manner appropriate for a prosthetic suction liner.

The reinforcing fibers 26 may be a circular knit textile formed of relatively non-distendable interlocked fibers (at least within the load ranges contemplated for use in a prosthetic suction liner) wherein the knit construction is such that the layer 26 strongly resists elongation in a longitudinal direction while being freely distendable laterally in a radial direction when it is embedded in the composite elastic layer 12. Any appropriate reinforcement matrix that would provide such properties could be used for layer 26, but as a practical matter a circular knit glass fiber or Nylon material is appropriate, provided it has the anisotropic properties described above.

The textile layer 14 is normally air permeable and is usually formed from a flat knit elasticized fabric that has been rolled into a tube and stitched along abutting side edges along the length of the tube. The inside surface of the fabric layer 14 facing the composite elastic layer 12 is coated with a thin layer of cured silicone elastomer 24 that is partially embedded in the fibers of the textile 14 without completely penetrating the textile 14. The silicone elastomer layer 24 is cured while embedded in the textile so that it is firmly adhered to the textile and preferably renders the textile and silicone layer 24 impermeable to air. The thin coating of silicone elastomer 24 provides a good bonding surface for the composite elastic layer 12 described above.

Preferably, the silicone layer 24 is obtainable under Product No. CF15-2188 from NuSil Technology of Carpinteria, Calif. Physical properties of the combined composite elastic layer 12, coating 24 and elasticized fabric 14 include a tensile strength greater than 1 Pa, preferably greater than 2 Pa; and a 100% modulus of 5 to 300 kPa, preferably 55 kPa.

The distal end cap 18 may be formed of a silicone elastomer including 98% by weight silicone rubber, type MED-4950 or type MED-4050 or type CF15-2188, all available from NuSil Technology, with the balance (2%) constituted of a color mixture, for example a color powder blended from 12.5 parts Lucas color No. 2408, 12.5 parts Lucas color No. 2439 and 75 parts Lucas color No. 2510 all obtainable from Fr. Schoenfeld GmbH and Co. include: the material uses a platinum cure system; a press cure time of 50 minutes at 150° C.; durometer 45–55; tensile strength 1000 psi (6.9 Mpa); elongation 400%; and a tear strength 230 ppi (40.3 kN/M).

Figure 5:
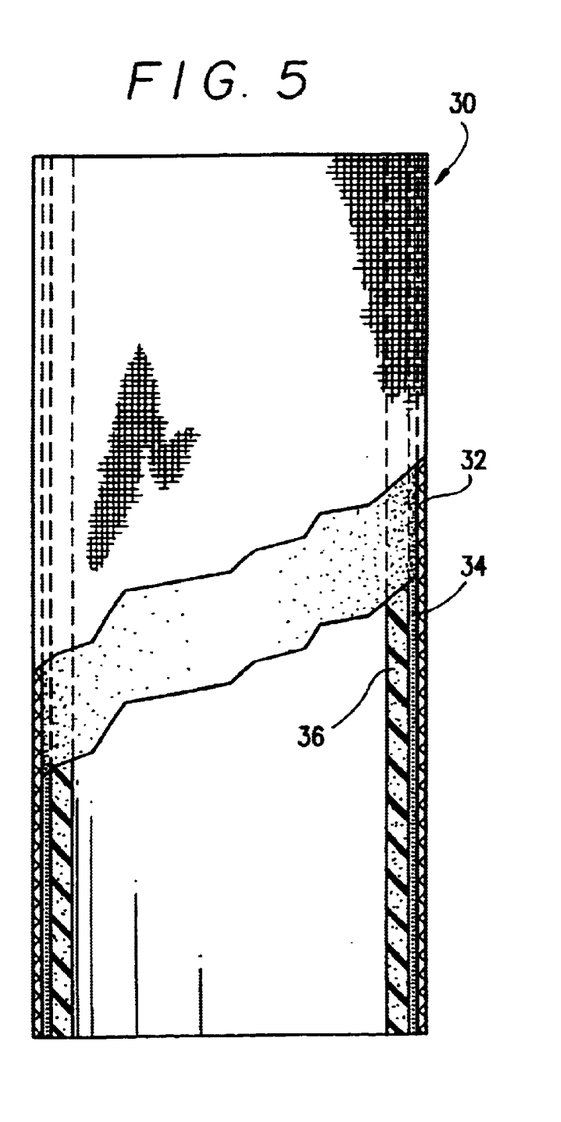
FIG. 5 shows a tubular sealing sleeve formed by using a coating process according to the present invention.

As illustrated in FIG. 5, a sealing sleeve 30, for example a sleeve capable of sealing the gap between the upper end of a prosthetic socket and a residual limb as illustrated in U.S. Pat. No. 5,571,208 includes an outer textile layer 32 that is an elasticized, porous or air permeable fabric on which a continuous cured silicone coating 34 has been applied and bonded thereto in the same manner as the coating 24 attached to the layer 14 of the suction sleeve material as illustrated in FIGS. 1–4 and described above.

The interior surface of the sleeve 30 includes a composite elastic material 36 formed in the same manner as the composite elastic layer 12 illustrated in FIGS. 1–4 and described above. The thickness of the composite elastic material 36 may be adjusted to fit the requirements of a sealing sleeve. The composite elastic layer 36 is intimately bonded and adhered to the coating 34. The combined assembly of the textile 32, coating 34 and composite elastic layer 36 is fully distendable both radially and longitudinally in accordance with the requirements of a sealing sleeve for prosthetic applications.

The outer fabric layer 32, in a preferred embodiment, may be a circular rib knit fabric made of 95% Nylon and 5% Lycra, knit as a 1×1 rib using 220 needles per 2.5 cm for a 12 cm width tube and 264 needles per 2.5 cm for a 14 cm tube. This fabric may be obtained from RX-Textile of Monroe, N.C.

A preferred form of the suction liner made with the composite elastic material layer 12 is illustrated in FIGS. 6–10 (the fabric is omitted in the views as being nonessential). The composite elastic material including the cured silicone elastomer layer with silicone oil and hollow microspheres and outer fabric is molded or formed as a tapered suction liner 40 having a closed distal end 42 of uniform thickness, an external profile 44 (see FIG. 10) that is circular with the radii of curvature of the external surface 44 centered on a first central longitudinal axis 46 extending through the suction liner 40. The geometry of such suction liner is illustrated in FIGS. 6–10. Moreover, the following table 1 describes the variables shown in FIGS. 6–10 and also describes typical values of some of the variables for different size suction liners listed in the left column of the table entitled "Typical Values of Variables".

TABLE 1

VARIABLE DESCRIPTION

| Variable name | Description |
| --- | --- |
| Angle | Angle of socket opening |
| H_fl_prox | Height of flange in proximal area |
| HH1 | Height to flange in distal area |
| HH2 | Height of flange in distal area |
| HH3 | Height of second cut |
| HHtot | Total height of socket |
| Hst | Height from radius to start of distal flange |
| Offset | Offset in lathe |
| Rrad1 | Radius on Distal end |
| RRad2 | Radius on proximal end |
| Tha | Thickness in anterior area |
| Thp | Thickness in posterior area |
| Thtop | Thickness of socket in top |

TYPICAL VALUES OF VARIABLES

| Size | Rrad1 | HH1 | HH2 | HH3 | Hhtot | RRad2 | Tha | Angle | Hfh prox | Offset | Thp | Hst | Thtop |
| --- | --- | --- | --- | --- | --- | --- | --- | --- | --- | --- | --- | --- | --- |
| 12 | 19 | rrad1 + Hst | 80 | Hhtot-HH1-Tha | 450 | 44.1 | 6 | 3 | 40 | 3 | 3 | 20 | 1 |
| 14 | 22.5 | rrad1 + Hst | 80 | Hhtot-HH1-Tha | 450 | 48.1 | 6 | 3 | 40 | 3 | 3 | 20 | 1 |
| 16 | 25.5 | rrad1 + Hst | 80 | Hhtot-HH1-Tha | 450 | 51 | 6 | 3 | 40 | 3 | 3 | 20 | 1 |
| 18 | 28.5 | rrad1 + Hst | 80 | Hhtot-HH1-Tha | 450 | 53.8 | 6 | 3 | 40 | 3 | 3 | 20 | 1 |
| 20 | 31.5 | rrad1 + Hst | 80 | Hhtot-HH1-Tha | 450 | 56.7 | 6 | 3 | 40 | 3 | 3 | 20 | 1 |
| 21 | 33.5 | rrad1 + Hst | 80 | Hhtot-HH1-Tha | 450 | 58.6 | 6 | 3 | 40 | 3 | 3 | 20 | 1 |
| 22 | 35.5 | rrad1 + Hst | 80 | Hhtot-HH1-Tha | 450 | 60.5 | 6 | 3 | 40 | 3 | 3 | 20 | 1 |
| 23.5 | 37.5 | rrad1 + Hst | 80 | Hhtot-HAH-Tha | 450 | 62.4 | 6 | 3 | 40 | 3 | 3 | 20 | 1 |
| 25 | 40 | rrad1 + Hst | 80 | Hhtot-HH1-Tha | 450 | 64.7 | 6 | 3 | 40 | 3 | 3 | 20 | 1 |
| 26.5 | 42.5 | rrad1 + Hst | 80 | Hhtot-HH1-Tha | 450 | 67.1 | 6 | 3 | 40 | 3 | 3 | 20 | 1 |
| 28 | 45 | rrad1 + Hst | 80 | Hhtot-HH1-Tha | 450 | 69.5 | 6 | 3 | 40 | 3 | 3 | 20 | 1 |
| 30 | 48 | rrad1 + Hst | 80 | Hhtot-HH1-Tha | 450 | 72.3 | 6 | 3 | 40 | 3 | 3 | 20 | 1 |
| 32 | 51 | rrad1 + Hst | 80 | Hhtot-HH1-Tha | 450 | 75.1 | 6 | 3 | 40 | 3 | 3 | 20 | 1 |
| 34 | 54 | rrad1 + Hst | 80 | Hhtot-HH1-Tha | 450 | 78 | 6 | 3 | 40 | 3 | 3 | 20 | 1 |
| 36 | 57 | rrad1 + Hst | 80 | Hhtot-HH1-Tha | 450 | 80.8 | 6 | 3 | 40 | 3 | 3 | 20 | 1 |
| 38 | 60.5 | rrad1 + Hst | 80 | Hhtot-HH1-Tha | 450 | 84.2 | 6 | 3 | 40 | 3 | 3 | 20 | 1 |
| 40 | 64 | rrad1 + Hst | 80 | Hhtot-HH1-Tha | 450 | 87.5 | 6 | 3 | 40 | 3 | 3 | 20 | 1 |
| 42.5 | 67.5 | rrad1 + Hst | 80 | Hhtot-HH1-Tha | 450 | 90.8 | 6 | 3 | 40 | 3 | 3 | 20 | 1 |
| 45 | 71.5 | rrad1 + Hst | 80 | Hhtot-HH1-Tha | 450 | 94.6 | 6 | 3 | 40 | 3 | 3 | 20 | 1 |

The suction sleeve 40 includes a circular curved inside anterior wall portion 50 having first radii of curvature centered on a second longitudinal axis of anterior curvature 52 extending longitudinally through the suction sleeve towards the anterior side of the first central axis 46 and a posterior wall portion 54 having second radii of curvature centered on a third longitudinal axis 56 located in the posterior direction relative to the central axis 46, said first, second and third longitudinal axes 46,52 and 56 all lying in a common longitudinally and transversely extending imaginary plane 60 (FIG. 10) bisecting the anterior and posterior wall portions 50,54 and wherein the second and third axes 52 and 56 are spaced apart a predetermined offset distance from each other on opposed sides of the first axis 46. Thus, this arrangement produces a posterior wall that is thinner than the anterior wall as shown in FIG. 10.

Figures 8, 9, 10:
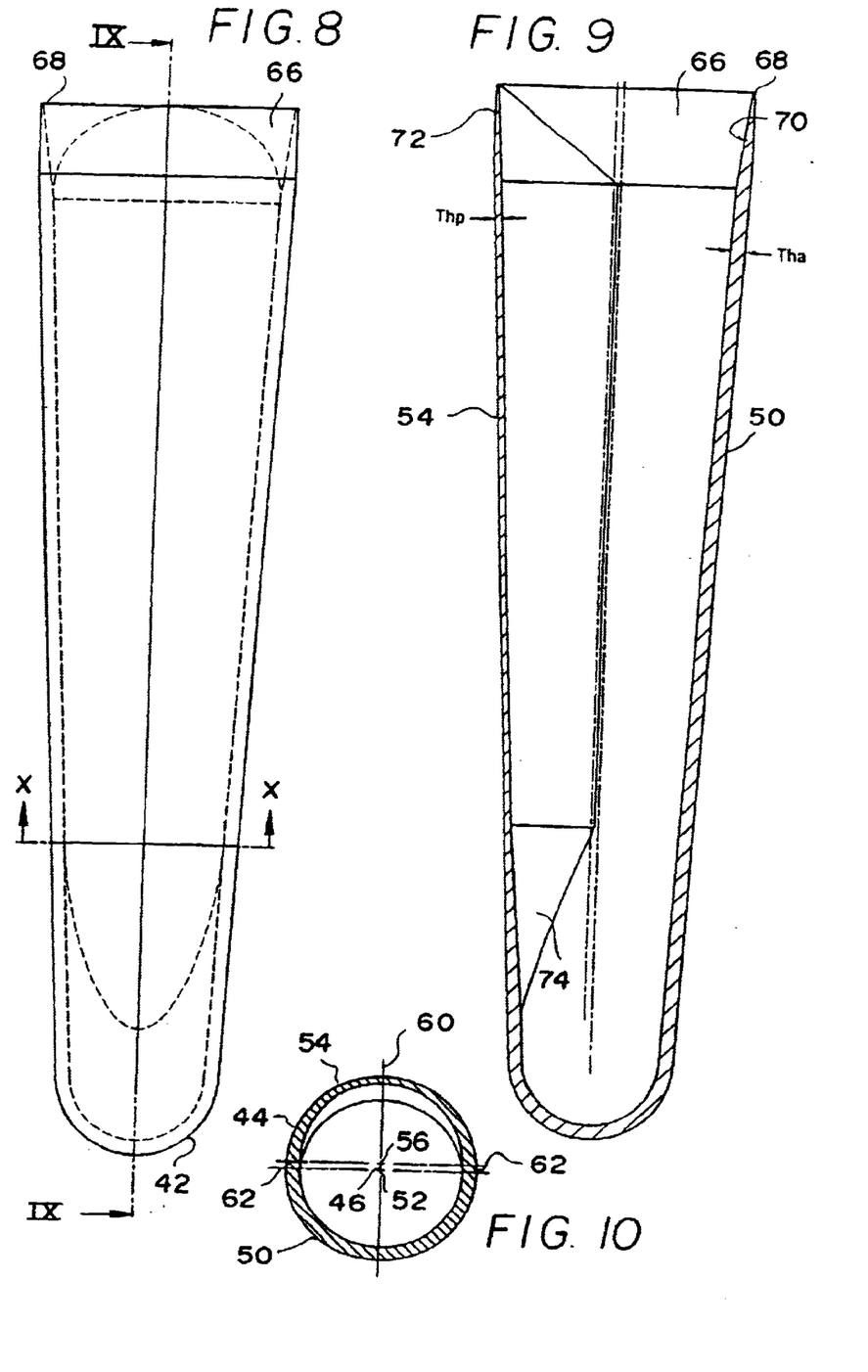

The anterior and posterior wall portions 50,54 intersect each other along inner diametrically opposed transition wall portions 62 that extend tangentially relative to the adjoining anterior and posterior wall portions along the sleeve length, so that the interior wall surface of the suction liner along the transition areas 62 are free of rapid changes in thickness, curvature or cross-section profile, as seen best in FIG. 10.

Figures 6, 7:
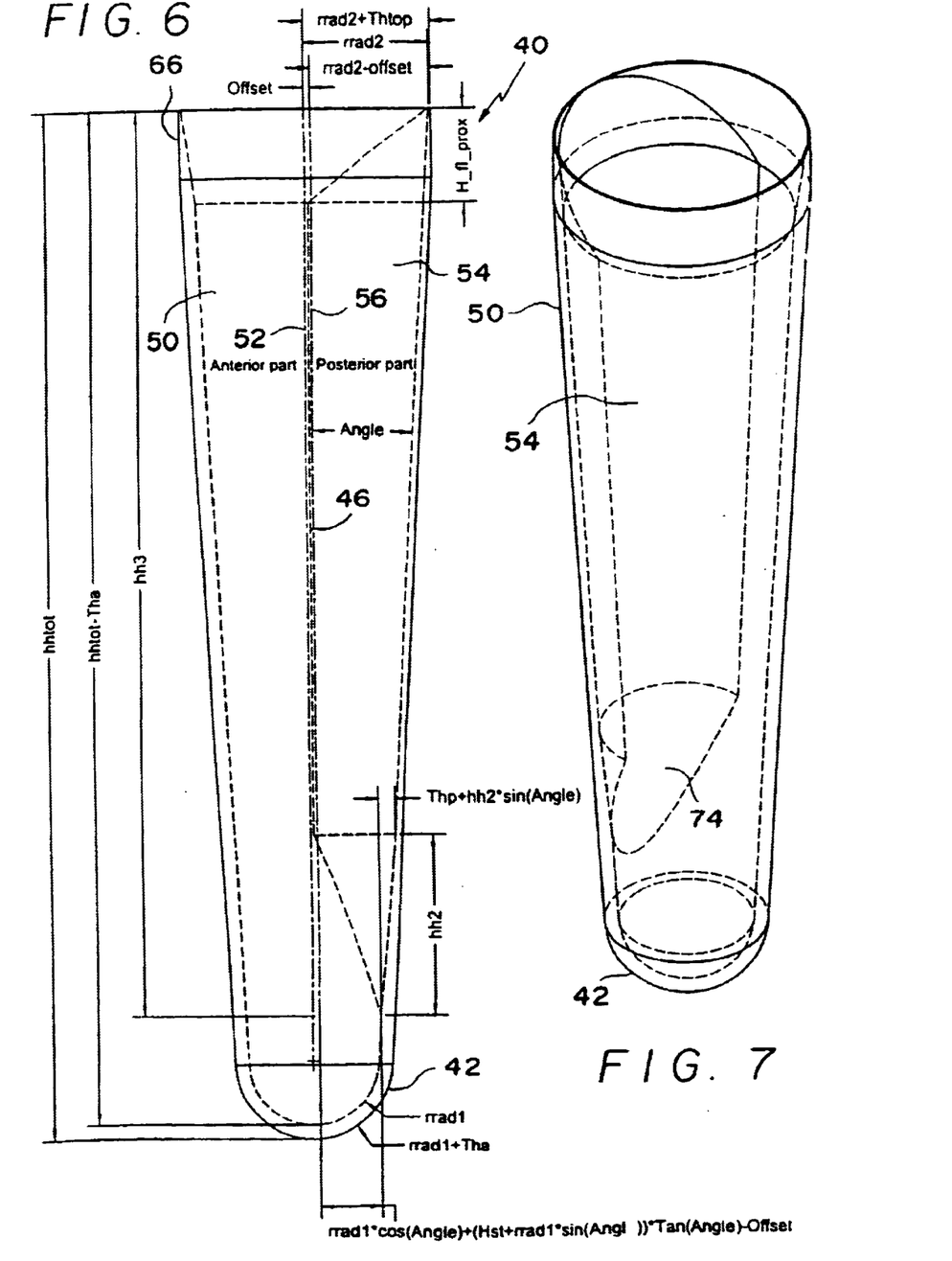
FIGS. 6–10 show the geometry of the cured silicone elastomer inner layer of a suction sleeve shown in FIG. 1.

In the example illustrated, the radii of curvature of the inside surfaces of the anterior and posterior portions of the sleeve are equal to each other along their respective second and third axes, as observable in FIG. 10. A formula for generating the interior profile of the suction sleeve shown in FIGS. 6–10 is indicated at the bottom of FIG. 6, and such formula is used to control a computer assisted machine tool (e.g., lathe) used to form a male mold element that shapes the inner profile of the liner.

At the proximal area of the suction sleeve 40 (the open end of the sleeve) a flange area 66 is provided wherein the thickness of the composite elastic material progressively thins as the top edge 68 is approached. The inside surface of the flange portion 66 of the anterior wall 50, as seen in FIG. 9, tapers inwardly as the top edge 68 is approached as shown at 70 and the outer surface of the proximal end of the flange portion 66 of posterior wall 54 also tapers inwardly as shown at 72 in FIG. 9. Preferably, the top edge 68 of the sleeve is relatively thin as compared with the thickness of the remainder of the sleeve.

The distal end 42 of the sleeve is spherical in curvature and joins the adjoining side wall of the sleeve along a tangent so as to provide a smooth interior and exterior contour as the sleeve transitions between the tapered conical upper portion and the spherically curved closed end portion 42. The thickness of the end portion 42 may be the same thickness as the anterior wall 50. The posterior wall 54 transitions from the same thickness as the anterior wall at the distal end of the sleeve to a thinner wall section over the length of the sleeve in which the thinner wall section is desired. A smooth transition area 74 is provided between the thinner posterior wall section 54 and the full thickness of the wall portion of the sleeve at the distal end of the sleeve.

The suction liner as illustrated in FIG. 1 may be made in accordance with the process described below using the apparatus also described below for carrying out the process.

Figures 11, 12, 13, 14, 15:
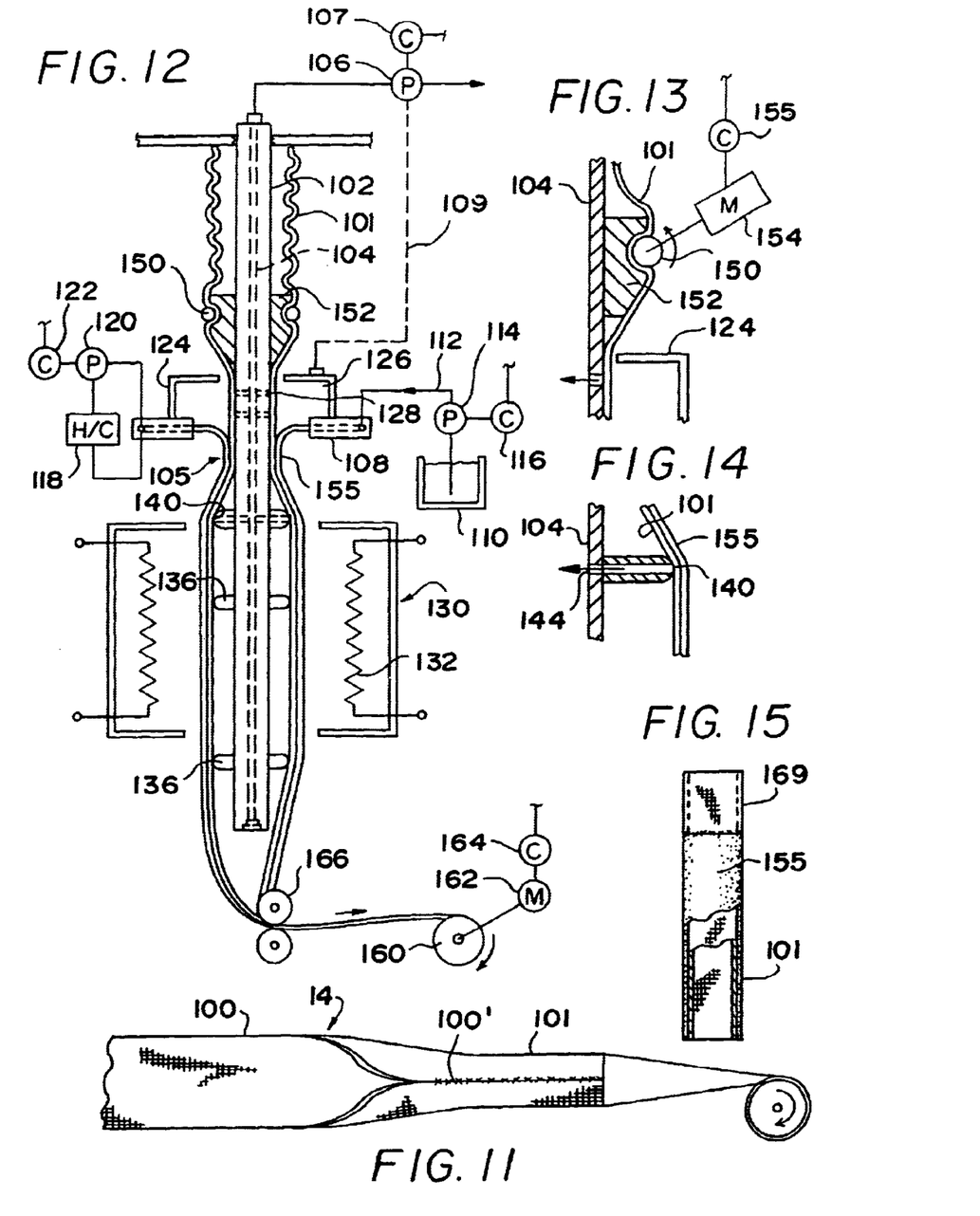
FIG. 11 is a schematic view of a flat section of elasticized fabric in process of being folded and stitched to form a length of tubular elasticized fabric.
FIG. 12 schematically shows a continuous coating system for applying a cast elastomer film onto one surface of the tubular substrate in a continuous process.
FIGS. 13 and 14 show details of the apparatus illustrated in FIG. 12.
FIG. 15 shows a reinforcement matrix stitched to one end of a length of elasticized fabric that has been coated with a continuous cured silicone elastomer film.

A textile layer corresponding to layer 14 is initially made as a flat strip 100 as illustrated in FIG. 11. The flat strip is rolled into a tubular form so that opposed side edges of the strip are abutted together and then stitched at 100' along the abutting edges to form continuous lengths 101 of tubular elasticized fabric that may be utilized in the external cover of a suction liner such as suction liner 10.

A continuous film casting device for coating the tubes 101 includes a vertically extending rod 102 having a conduit 104 extending therethrough in communication with a suction pump 106, the operation of which is controlled by a controller element 107 in a manner to be described in more detail below.

Along the length of the vertical rod 102, there is provided a casting zone 105 along which is located continuous annular film casting device 108 through which an uncured tubular elastomeric film or layer may be expressed as a continuous, generally vertical uninterrupted film generally coaxially surrounding the rod 102 or any substrate material that may be advanced along the surface of the rod 102 through the film casting device 108.

A source 110 of coating material to be expressed through the film casting device 108 is connected to the latter by means of conduit 112, pump 114 and a control system 116 for governing the operation of the pump 114.

The film casting device 108 may be provided with a heating and cooling system 118, which may include a circulating system for circulating a heating or cooling medium through the film casting device 108 by means of a pump 120 governed by a control system 122.

A suction or sub-atmosphere chamber 124 is connected to the upper surface of the film casting device 108 to create a sub-atmospheric pressure chamber 126 when a suction is applied to the chamber 126 via conduit 128. The conduit 128, for example, may be connected to suction pump 106 via conduit 104 during operation of the film casting device to create a sub-atmospheric pressure in chamber 126, or a separate suction line 109 may be used for this purpose.

The lower end of the rod 102 extends through a heating or curing zone including heating furnace 130 which may contain, for example, radiant or electrical heating elements 132 that provide a source of heat for curing a film expressed through the film casting device 108.

Annular tension control washers 136 spaced axially along the length of rod 102 are provided to control tension of a substrate coated in the apparatus described in a manner to be explained in more detail below.

An annular array of suction orifices 140 or the equivalent are provided on the rod 102 and which are in communication with air passages 144 which are in turn in communication with air passage 104 within rod 102. Orifices 140 may be incorporated in an annular member affixed to the rod 102 at a location where apertures 144 are provided in the rod 102 enabling communication between the orifices 140 and the passage 104. Suction applied by pump 106 can thereby be applied at orifices 140 over an area surrounding the rod 102.

Textile advancing drive elements 150 are provided adjacent the rod 102 above the suction housing 124 for cooperating with a relatively fixed guide element 152 affixed to rod 102. The drive element 150 is rotatable by a motor 154 operable under the control of a controller 55 connected to the motor. When a substrate is inserted between the drive element 150 and the seat 152, the substrate will be advanced along the rod 102 in accordance with the driving direction of the rotatable element 150.

The orifices in film casting device 108 for expressing or discharging a tubular film or coating material 155 supplied from source 110 is configured in accordance with desired properties of the film or coating to be applied by the coating system as shown. Relatively thin coatings may be expressed through a continuous annular slot provided in the film casting device 108 or relatively thick coatings may be applied in the same fashion.

The vacuum in chamber 126 is adjusted to provide initial contact between a film 155 expressed through the film casting device 108 and the substrate advanced through the film casting device in a manner to be described below. Subsequently, when the substrate is air permeable, the suction device 140 draws the uncured film material into the substrate to a desired extent, for example only partially through the substrate thickness if it is desired to maintain uncoated substrate on the opposed surface of the substrate advanced through the film casting device. Higher suction applied at suction device 140 could be applied if it was desired to fully penetrate a porous substrate advanced through the film casting device.

The heater 130 is regulated to fully cure a film expressed through the film casting device 108 and the time and temperature of such curing may be regulated by regulating the speed of advancement of the coated substrate through the heating device in accordance with known principles related to curing of curable films in coatings such as silicone elastomer, for example.

The operation of the film casting system as shown in FIG. 12 will now be explained in the context of coating an elasticized tubular fabric with a cured silicone elastomer film. A previously formed length of tubular, elasticized fabric such as porous or air permeable fabric length 101 is threaded vertically upwardly over rod 102 with a lower end of the fabric threaded over element 152, through suction chamber 126, through the film coating device 108, over suction device 140, through heater 130 and onto a take-up spool 160 that is rotatable at a controlled speed by motor 162 in accordance with signals received from controller 164. Idler rollers 166 may be provided to enable the direction of the coated fabric to be turned at the lower end of rod 102 to advance the fabric to the take-up spool 160.

With a length of fabric 101 thus threaded over rod 102, the fabric is drawn at a controlled speed downwardly over the rod 102 while suction chamber 106 is activated and an uncured tubular silicone elastomer resin film is expressed outwardly as a thin annular sheet of film from casting device 108 towards the fabric 101 that is drawn through the film casting device 108. Initially, the inner edge of the film expressed through the film casting device 108 may be manually adhered to the surface of fabric 101, whereupon the film 126 effectively closes the bottom of the suction chamber 126 so that the film is thereafter drawn inwardly by sub-atmospheric pressure communicated to the outer surface of the fabric 101 via the interstices of the fabric against the surface of the fabric uniformly over its entire periphery as the fabric is advanced through the film casting device 108.

The fabric is threaded through the advancing mechanism 150, 152 by rotating the roller 150 in a direction to advance the fabric downwardly over the rod 102. The positive feeding of the fabric 101 through the suction device 126 prevents undue tension from being applied to the fabric upon rotation of the take-up spool 160. It is desirable to maintain the fabric substrate in a relatively relaxed condition to the extent possible, although a pretension may be applied to the fabric if desired as it is advanced through the film casting device 108 or through the heater 130.

The suction device 140, as shown in detail in FIG. 14, draws the uncured and pliable continuous, uninterrupted elastomeric film layer intimately into contact with and adhered to the air permeable substrate fabric 14 to the extent desired for the specific application of the coated fabric.

The fabric with the uncured resin coating then passes through the heater 130 where the coating is cured for a desired time at a desired temperature, all dictated by the properties of the cast film to be cured, and in accordance with known principles.

Within the heater 130, the tension on the coated fabric is controlled by the annular tension control washer elements 136 which apply a predetermined frictional drag on the fabric on its inner side as it is advanced over the rod 102 and also maintain the fabric extended radially somewhat as it passes through the heater 130. The number of annular elements 136 may be adjusted in accordance with the fabric and the coating applied thereto.

The film casting device 108 may be selectively heated or cooled by using the heating and cooling system illustrated at 118,120,122. The degree of heating or cooling will depend upon the composition of the film to be cast on the surface of the fabric 101.

The resultant coated tubular fabric collected on spool 160 is now available to be used in a subsequent process to make a suction liner or may be available for any other application wherein a continuous cured coating applied to an elasticized tubular substrate is desired.

In this example, the film to be cast on fabric 101 corresponds to film 24 described previously and the fabric 101 corresponds to the fabric outer layer 14 of the silicone liner described above in FIGS. 1–4.

After coating of the elasticized fabric 101 using the apparatus described above, the coated fabric is cut into lengths as shown in FIG. 15 and a length of tubular reinforcement matrix material 169 is affixed, for example by sewing, to the end of the coated fabric. The matrix 170 may correspond to layer 26 in the suction liner of FIG. 1. Preferably the reinforcement matrix comprises interlocked fibers such as a circular knit tubular fabric that strongly resist longitudinal elongation but readily distends radially.

Individual lengths of the coated fabric and reinforcement matrix are then prepared to receive a distal end cap (to be described below) that will be molded to one end of the coated length of fabric 101 to close said end and to embed a portion of the matrix 170 in the interior of the coated tubular fabric, as will become evident following a review of the description of the distal end cap molding apparatus shown in FIG. 16.

After coating of the elasticized fabric 101 using the apparatus described above, the coated fabric is cut into lengths as shown in FIG. 15 and a length of tubular reinforcement matrix material 169 is affixed, for example by sewing, to the end of the coated fabric. The matrix 169 may correspond to layer 26 in the suction liner of FIG. 1. Preferably the reinforcement matrix comprises interlocked fibers such as a circular knit tubular fabric that strongly resist longitudinal elongation but readily distends radially.

Figure 16:
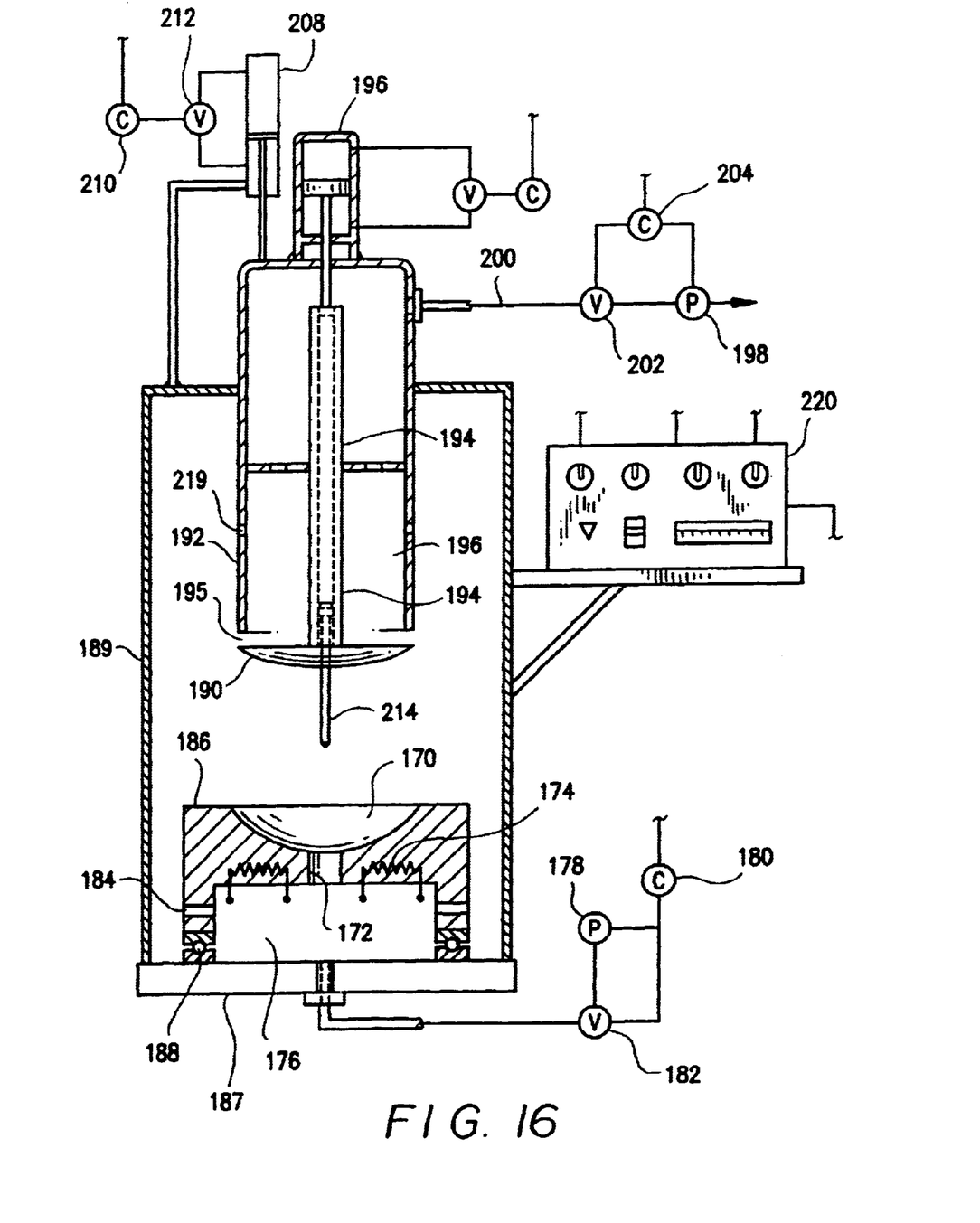
FIG. 16 shows a molding device for molding a distal end cap onto the length of tubular elasticized fabric that has been previously coated and provided with a tubular length of reinforcement matrix at one end thereof.

In FIG. 16, a compression molding apparatus is illustrated for use in molding a distal end cap on one end of a length 101 of coated elasticized fabric with a reinforcement matrix 169 attached thereto. The molding apparatus includes a lower female mold cavity 170 configured to form an external shape on a distal end cap to be molded in the cavity and including a central guiding aperture 172, heating elements 174, preferably electrically energized, and a pressure chamber 176 that is in communication with a pneumatic pump 178 that is controllable by controller 180 in combination with a shut-off valve 182 that selectively pressurizes pressure chamber 176. Pneumatic pressure orifices 184 are spaced peripherally around the support 186 for the female mold 170.

The support 186 is rotatably mounted on a base 187 by means of bearings 188 so that the female mold support 186 may be rotated about an axis of rotation relative to the base 187 and the upper part of the molding device to be described below. Vertical support members 189 are schematically illustrated extending between the base 187 and the upper part of the molding device. The support members 189 may be rods or pillars with open areas between them to provide access to the female mold 170 and the upper part of the molding device.

The upper part of the molding device supported above the female mold 170 includes a male mold plug and clamping element 190 and a cooperating clamping cylinder 192 that slidably supports the male mold and clamping device 190 for reciprocal movement relative to the clamping cylinder 192. The mold and clamping device 190 is supported, for example, by a rod 194 or equivalent that is connected to a pneumatic cylinder 196 that is operable to control movement of the male mold and clamping element 190 towards and away from the distal end of the clamping cylinder 192 to effectively open or close the distal or lower end of the clamping cylinder 192.

The interior of clamping cylinder 192 is provided with a suction chamber 196 that communicates with a suction pump 198 via conduit 200 and shut-off valve 202. Pump 198 and shut-off valve 202 are operated under the control of a controller 204 such that a suction can be applied to suction chamber 196 by pump 198 selectively to create an inflow of air between the mold and clamping device 190 and the distal end of the clamping cylinder 192 through a gap 195.

The entire assembly of the clamping cylinder 192 and the mold and clamping device 190 may be reciprocally moved towards and away from the female mold 170 by a second pneumatic or hydraulic cylinder 208, the operation of which is controlled by a controller 210 and appropriate valving 212, whereby the clamping cylinder 192 and the mold and clamping device 190 may be advanced into cooperation with the female mold 170 to create a mold cavity between the bottom surface of the mold and clamping device 190 and the surface of the female mold 170.

A guide rod and orifice plug 214 optionally extends centrally through the male mold and clamping device 190 for cooperation with the guide opening 172 in the female mold 170 when it is desired to maintain an aperture in a distal end cap to be molded between the male and female molds 190,170. Such an aperture is desired if a prosthetic connector is to be molded into the end cap.

The various pumps, valves and controllers, as well as the heating elements 174 all may be controlled and operated from a central control panel 220 using conventional control technology including digital computer processors.

Figure 17:
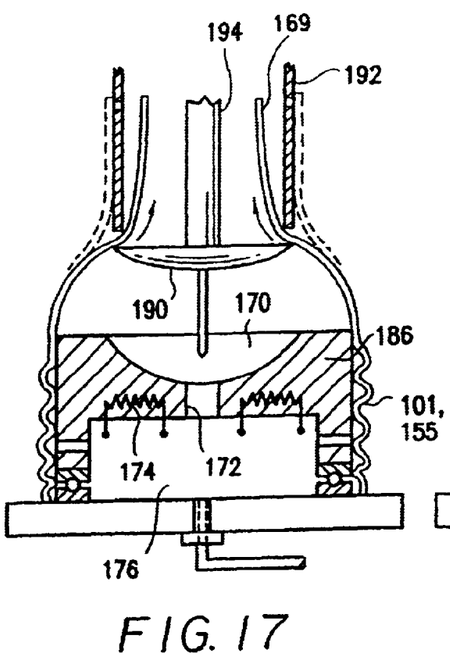
FIGS. 17–21 schematically illustrate a procedure for molding a distal end cap onto the tubular fabric using the apparatus shown in FIG. 17.

The operation of the molding device described in FIG. 17 will now be described in conjunction with FIGS. 18–22 when it is desired to mold an end cap on a coated elasticized fabric with a prosthetic connector and a distension controlling reinforcement matrix as previously described. Initially, a length of the coated elasticized fabric 101 with a reinforcement matrix 169 attached thereto as shown in FIG. 15 is threaded over the female mold support 186 with the free end of the reinforcement matrix 169 threaded over the distal end area of the clamping cylinder 192, as illustrated in FIG. 17. The mold and clamping device 190 is in the extended position thereby exposing the gap 195 between the mold and clamping device 190 and the distal end of clamping cylinder 192. A suction is then applied to the suction chamber 196 by pump 106 which draws in the free end of the reinforcement matrix 169 through the gap 195.

Figure 18:
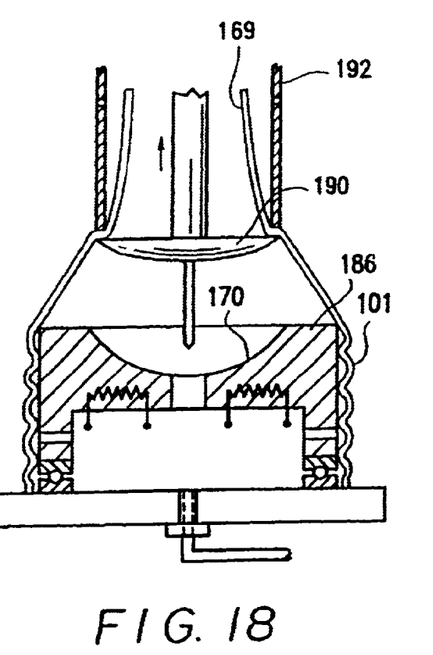

The mold and clamping element 190 is then moved to its upper or closed position relative to the clamping cylinder 192 to effectively close the gap 195 and to clamp the free end of the reinforcement matrix 169 between the mold and clamping device 190 and the clamping cylinder 192, as illustrated in FIG. 18.

Figure 19:
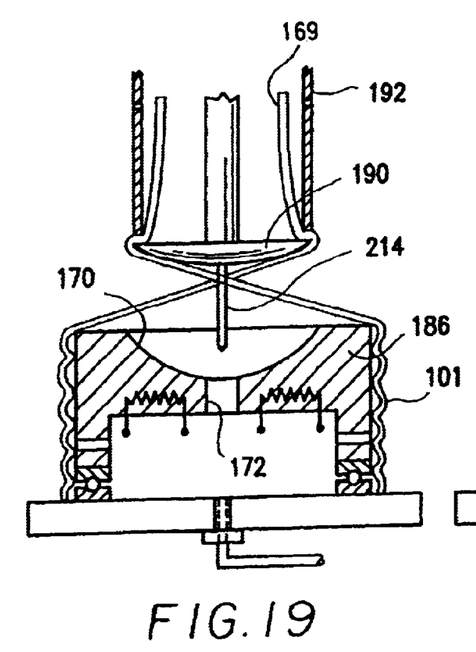

The female mold support 186 is then rotated ¼ turn or so relative to the base 187 to introduce a twist constriction 218 in the tubular reinforcement matrix 169 that effectively forms a closure at the one end of the length of coated elasticized fabric 101 and leaves a free tubular length of reinforcement matrix 169 within the clamping cylinder 192. The rod element 214 in this example extends through the central area of the twisted section 218 of reinforcement matrix 169.

Figure 20:
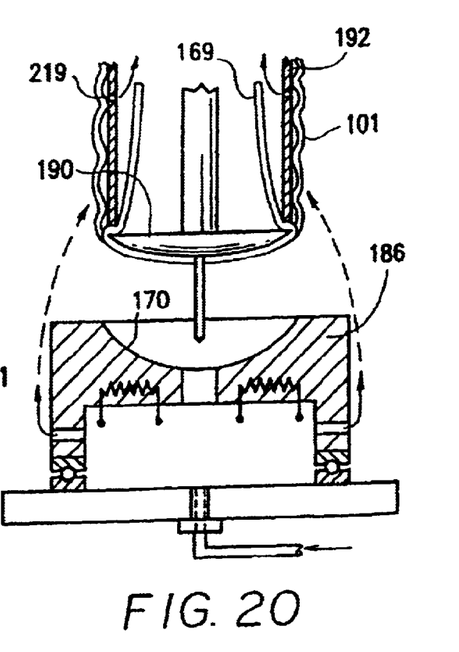

As shown in FIG. 20, a sudden pressure is then applied to pressure chamber 176 that blows the length of coated elasticized textile outwardly and upwardly over the external surface of the clamping cylinder 192, which may be provided with suction orifices 219 to assist in this procedure as seen in FIG. 20.

Figure 21:
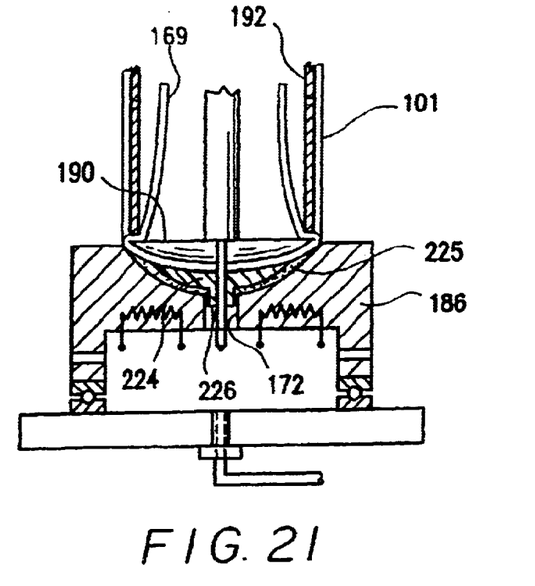

A rigid prosthetic connector "umbrella" element 224 is next primed or coated with an uncured elastomer that forms an intimate bond with the connector element and with the elastomer to be used for the distal end cap to be molded in the cavity to be provided between the male mold and clamping element 190 and the female mold 170. The thus primed and coated prosthetic connector element 224 is placed in the female mold 170 so that it is spaced away from the bottom of the mold surface with a connector portion thereof 226 extending through aperture 172. A premeasured portion 225 of uncured elastomer material (which may be the same as the primer) is then placed in the female mold cavity 170 on the connector element 224 and thereafter the clamping cylinder 192 and the associated mold and clamping device 190 with the coated elasticized fabric 101 and reinforcement matrix 169 is advanced towards the female mold 170 to compress and shape the uncured elastomer material in the mold cavity so that it conforms on one side to the surface of the female mold 170 and on its other side to the surface of the male mold and clamping element 190. In this process, the prosthetic connector 224 becomes totally embedded in the silicone material in the mold cavity so that it is completely covered by the elastomer. This is illustrated in FIG. 21, for example.

Figure 22:
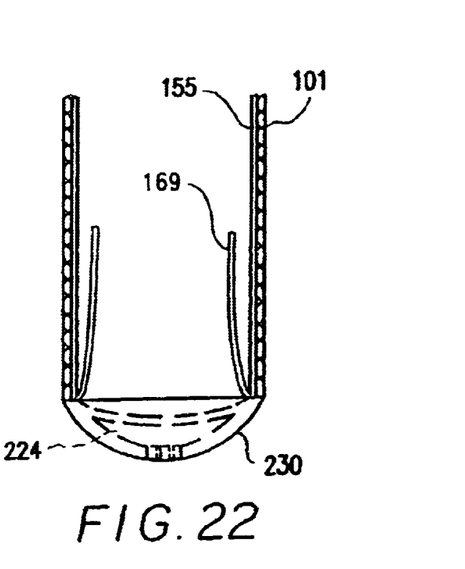
FIG. 22 is a detailed view showing the distal end of an assembly of elasticized tubular fabric coated with a continuous silicone elastomer film on the inner surface thereof, a reinforcement matrix, a distal end cap and an embedded prosthetic connector in the distal end cap.

The heater element 174 is activated at the appropriate time to heat the female mold 170 to an appropriate curing temperature for the silicone elastomer used to form the distal end cap and the priming elastomer applied on the prosthetic connector 224. The elastomer is then cured to produce a relatively firm distal end cap 230 as shown in FIG. 22, with a free length of reinforcement matrix 169 within the coated elasticized fabric 101. The distal end cap 230 bonds together the twisted reinforcement matrix 218 while the male and female molding surfaces together shape the inside and outside contours of the distal end of the coated fabric 101. The elastomer selected for the end cap 230 provides desired properties for the distal end cap as part of a prosthetic suction liner.

Figure 23:
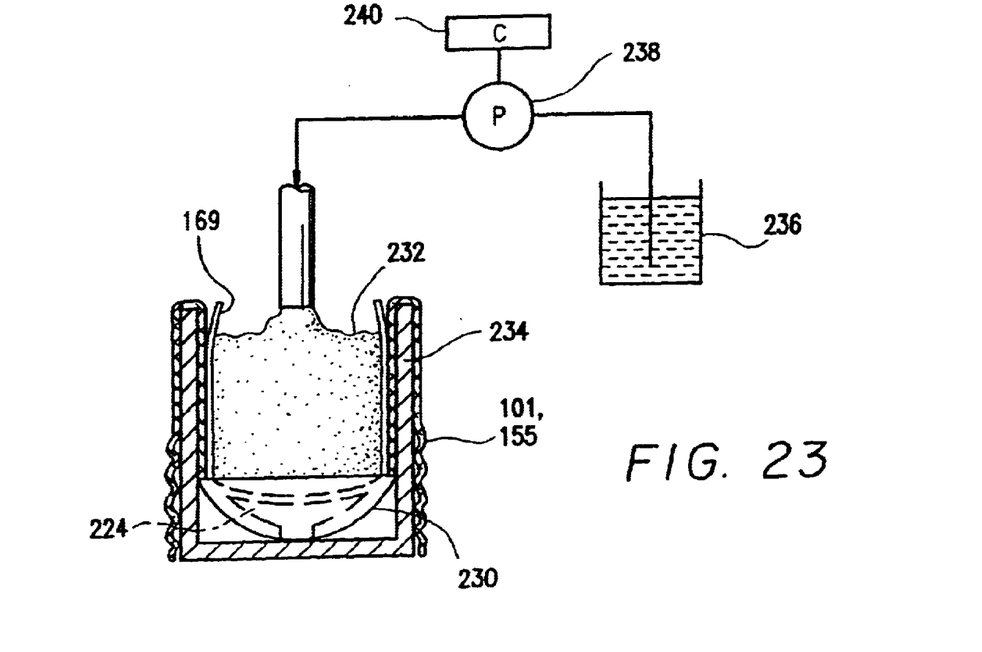
FIG. 23 schematically illustrates a procedure to dispense a predetermined quantity of uncured silicone elastomer into the closed end of the preformed assembly illustrated in FIG. 23.
Figures 24, 25, 26:
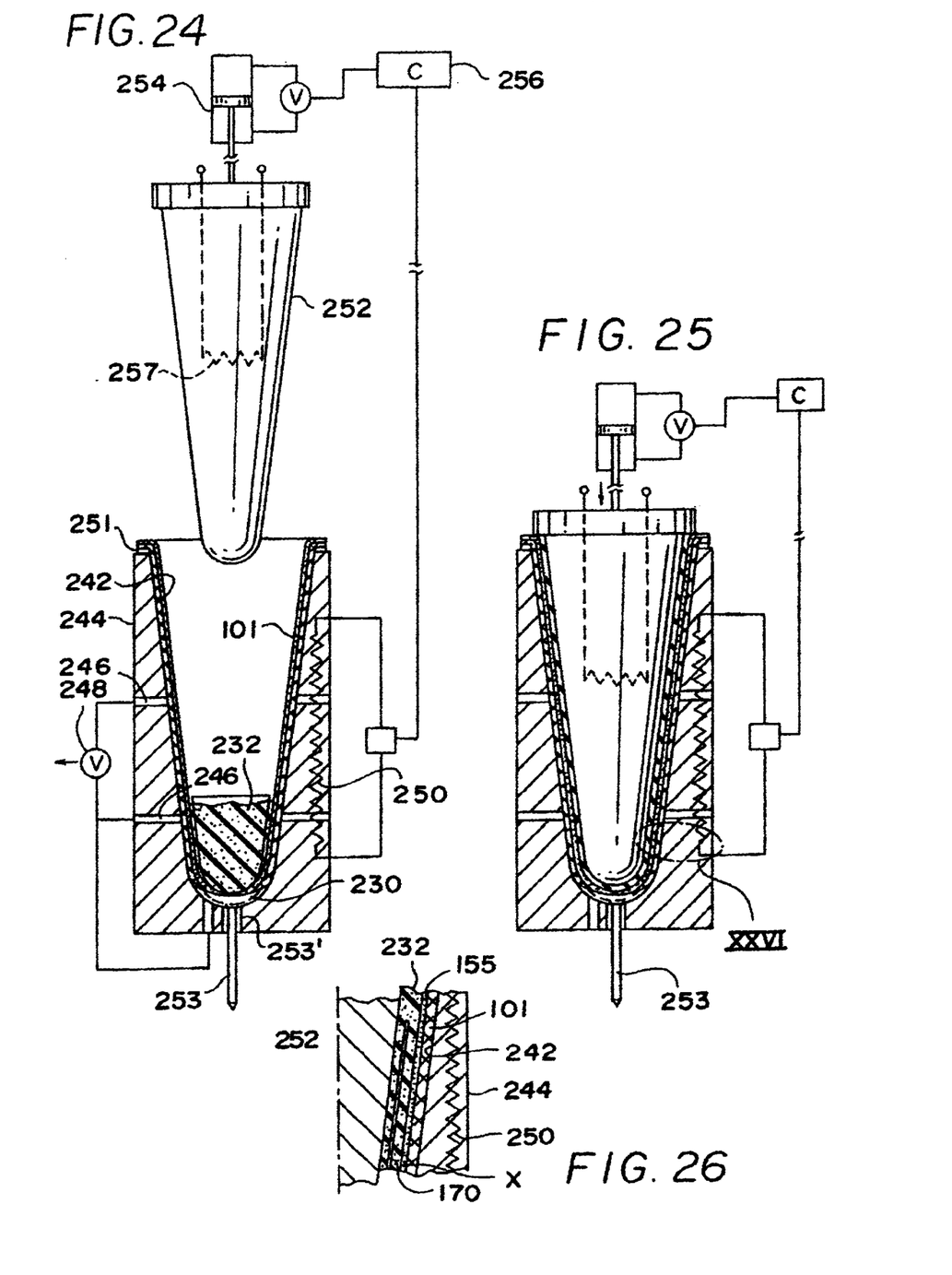
FIG. 24 shows a cold forging system utilizing a female mold cavity and a male mold element that are brought together to form a mold cavity into which previously inserted uncured silicone elastomer is cold forged to completely fill the mold cavity.
FIG. 25 shows the die system illustrated in FIG. 24 in a closed condition.
FIG. 26 shows the detail XXVI in FIG. 25.

The pre-formed assembly of coated tubular elasticized fabric 101, end cap 230 and reinforcement matrix 169 are then placed in a holder 234 as shown in FIG. 23 to expose the internal distal end of the length of coated fabric 101 and the reinforcement matrix 169 so that a pre-measured quantity of uncured elastomer liner resin material 232, for example, a silicone elastomer corresponding to the composite elastic material 12 shown in FIG. 1, can be dispensed into the open distal end as shown in FIG. 24. A source of the silicone elastomer resin is provided at 236 and a precision measuring pump 238 is operated via controller 240 to dispense a precise quantity of uncured elastomer 232 into the holder 234 and within the open distal end of the length of tubular elasticized fabric 101 that has been closed by the end cap 230.

The partially filled pre-form is now placed in a female molding or shaping die cavity 242 as shown in FIG. 24 with the length of coated fabric 101 fully extended over the length of the female die cavity 242. The female die cavity 242 is defined within a female die support structure 244 that may include suction orifices 246 to which a suction may be applied via valve 248 to draw the pre-formed coated elasticized fabric 101 and the distal end cap 230 into close conformity with the female die cavity 242. The support 244 includes a heater 250 that may be energized to raise the temperature of the female die support up to the curing temperature of the elastomer deposited in the distal end of the coated fabric sleeve 14.

A male die element or plug 252 is reciprocally mounted relative to the female die support 244 so as to be axially movable into and out of the cavity defined by the female die 242. A pneumatic or hydraulic cylinder arrangement 254 may be provided to advance the male die element 252 towards and away from the female die cavity 242 under the control of a controller 256 that may be integrated with the controller for the heater 250.

The external contour of the male die 252 is configured to provide a defined shape to produce a die cavity that results when the male die 252 is fully advanced towards the female die cavity 242 to form a die cavity as shown in FIG. 25. As the male die 252 advances into female die cavity 242, the uncured elastomer 232 is cold forged or driven into the die cavity between the male die 252 and the inner walls of the female cavity 242 progressively from the distal end of the pre-formed coated fabric and distal end cap to the proximal open end of the tubular fabric 101. The external surface of the male die 252 is contoured to define the internal shape of the elastomer material occupying the die cavity between the male die 252 and the female die cavity 242 while the female die cavity 242 is shaped to define the external contour of the fabric 101 to be joined with the elastomer in the mold cavity. The contour of the male die 252 also includes appropriate surface areas designed to enhance the uniform flow of uncured elastomer from the distal end of the pre-form to the proximal end thereof to ensure that the die cavity between the male and female die elements is completely and uniformly filled with the uncured elastomer material that previously was introduced into the tubular elasticized fabric 101 in a quantity sufficient to fill the die cavity.

To assist in guiding the length of coated fabric 101 into the female die cavity 242, a guide pin 253 having a threaded proximal end may be threaded into the prosthetic connector 224 prior to insertion of the fabric length 101 into the female die cavity. An aperture 253' is provided in the bottom of the support 244 to receive the guide pin 253 as the fabric length 101 is lowered into the female die cavity.

To assure uniform lengths of finished cold forged products, a locking ring 251 may be provided at one end of the fabric sleeve 101 that cooperates with the male die 252 to limit the length of the cold forged liner formed from the uncured silicone elastomer 232 when the male and female dies are brought together.

The heater 250 is activated at the appropriate time to cure the elastomer 232 in the die cavity for an appropriate length of time and at an appropriate temperature in accordance with the elastomer material selected to fill the mold cavity. Heaters 257 may be used in the male die 252 as well.

FIG. 26 shows an enlargement of a detail of the female die cavity 242, the heater 250, the coated fabric 101, the coating 155 on the fabric and the innermost layer 232 of elastomer containing an embedded reinforcement matrix and the position of the male die 252. Upon curing of the elastomer in the mold cavity, the male die 252 is withdrawn and the now-;fully integrated assembly of fabric 101, elastomer coating 155, and innermost elastomer layer 232 is removed from the female mold 242. The guide pin is then removed, leaving a fully formed suction liner corresponding to suction liner 10 in FIG. 1 ready for final detailing and eventual use.

When the innermost layer of elastomer 232 is constituted of the composite elastic material described above in connection with FIGS. 1–4, the male and female dies may be heated to a temperature of 100° C. and the elastomer may be cured for a cure time of 6 minutes.

The exterior contour of the male die 252 may be shaped in accordance with the inner peripheral contour of layer 12 of suction sleeve 10 as described in connection with FIGS. 6–10 as described previously.

While a specific embodiment of the inventive process and apparatus constituting the inventive subject matter have been described previously, it should be understood that various modifications to the process and apparatus can be made without departing from the spirit and scope of the invention.

The tubular fabric 101 may be produced in various lengths with or without a longitudinal seam and instead of a reinforcement matrix 169, any appropriate material can be utilized to form a twisting closure in the apparatus shown in FIG. 16, including the fabric 101 itself if no matrix is used.

The coating apparatus of FIGS. 12–15 may be utilized to coat any tubular material, including a non-porous or non-permeable tubular material. When non-porous material is coated, the suction applied in suction chamber 126 is adjusted to ensure appropriate adhesive to the exterior surface of the moving tubular substrate and the suction orifices 140 do not need to be used. Likewise, the tension controlling elements 136 may be adjusted to accommodate the specific tubular substrate to be coated in the apparatus.

The premeasured quantity of uncured silicone elastomer could be directly deposited into the open tube 101 after the latter has been set into the female die cavity 242.

Other various departures from the specific embodiment described above can be envisioned within the skill of the person skilled in the art and it is to be understood that the specific steps and apparatus disclosed herein are to be exemplary only.

What is claimed is:

1. A preform for a prosthetic suspension sleeve comprising:
    a tubular sleeve comprising an elasticized fabric, said tubular sleeve including a distal end;
    a distal end cap molded on and closing the distal end of the tubular sleeve;
    a tubular matrix reinforcement element secured coaxially to the distal end of the sleeve and having a portion embedded in the distal end cap and a portion extending freely within a distal end area of the sleeve.

2. A preform as claimed in claim 1, including a prosthetic umbrella connector element embedded in the distal end cap.

3. A preform as claimed in claim 1, said sleeve member having an inner wall, and including a continuous, uninterrupted cured elastomeric resin layer on the inside wall surface of said sleeve member.

4. A preform as claimed in claim 3, wherein said film coating and distal end cap comprise silicone elastomer material.

5. A preform as claimed in claim 1, wherein said matrix reinforcement element is circular knit fabric material selected from the group consisting of glass fiber and Nylon.

6. A preform for a prosthetic suspension sleeve comprising:

a tubular sleeve comprising elasticized fabric and including a distal end;

a tubular matrix reinforcement element secured coaxially to the distal end of the sleeve, said matrix reinforcement element comprising interlocked fibers that are arranged so that the matrix reinforcement element is porous and strongly resists elongation in the sleeve longitudinal direction but is readily elastically stretchable in transverse radial directions;

said elasticized fabric of said tubular sleeve having an inner wall coated with an uninterrupted, cured silicone elastomer layer, said layer only partially penetrating the elasticized fabric.

* * * * *